(12) United States Patent
Rothstein et al.

(10) Patent No.: US 8,998,933 B2
(45) Date of Patent: Apr. 7, 2015

(54) SURGICAL FASTENING CLIPS, SYSTEMS AND METHODS FOR PROXIMATING TISSUE

(75) Inventors: Paul T. Rothstein, Elk River, MN (US); Cynthia T. Clague, Minnetonka, MN (US); Michael M. Green, Forest Lake, MN (US); Damian A. Jelich, Cottage Grove, MN (US); Eric A. Meyer, Andover, MN (US); Mark T. Stewart, Lino Lakes, MN (US); Chris M. Coppin, Spokane, WA (US); Rany Huynh, Charlestown, MA (US); Mark W. Torrianni, San Juan Capistrano, CA (US); Asha S. Nayak, Sunnyvale, CA (US); John R. Liddicoat, Minneapolis, MN (US); Timothy G. Laske, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 1585 days.

(21) Appl. No.: 12/039,629

(22) Filed: Feb. 28, 2008

(65) Prior Publication Data
US 2009/0222026 A1 Sep. 3, 2009

(51) Int. Cl.
*A61B 17/10* (2006.01)
*A61B 17/00* (2006.01)
*A61B 17/064* (2006.01)
*A61B 17/08* (2006.01)

(52) U.S. Cl.
CPC ... *A61B 17/0057* (2013.01); *A61B 2017/00243* (2013.01); *A61B 2017/00575* (2013.01); *A61B 2017/00623* (2013.01); *A61B 2017/00867* (2013.01); *A61B 2017/0649* (2013.01); *A61B 2017/081* (2013.01)

(58) Field of Classification Search
USPC ............ 606/139, 151, 213, 232, 74–75, 144, 606/148, 153, 157–158, 142, 215, 216; 411/457–460, 483; 24/112, 18, 131 R, 24/119 R, 115 N
See application file for complete search history.

(56) References Cited

U.S. PATENT DOCUMENTS

| | | | | |
|---|---|---|---|---|
| 4,741,330 | A | * | 5/1988 | Hayhurst ...................... 606/144 |
| 4,898,156 | A | * | 2/1990 | Gatturna et al. .............. 606/139 |
| 4,899,743 | A | * | 2/1990 | Nicholson et al. ............ 606/139 |
| 5,002,563 | A |   | 3/1991 | Pyka et al. |
| 5,007,921 | A | * | 4/1991 | Brown .......................... 606/221 |
| 5,108,420 | A | * | 4/1992 | Marks ............................ 606/213 |

(Continued)

FOREIGN PATENT DOCUMENTS

| | | |
|---|---|---|
| WO | 96/03925 | 2/1996 |
| WO | 98/29040 | 7/1998 |
| WO | 00/07506 | 2/2000 |

*Primary Examiner* — Gregory Anderson

(57) ABSTRACT

A surgical fastener clip for proximating tissue, the clip providing an undeflected state in which the clip comprises a center portion, a first leg, and a second leg. The center portion has a perimeter defining a circle-like shape. The legs project outwardly relative to the perimeter from a point of departure to a tip. Extension of each of the legs relative to the perimeter defines an identical wind direction that is either clockwise or counterclockwise. The clip optionally includes a linear cross-member extending across the perimeter. The surgical clip can be formed by a wire that is partially wound onto itself in a spiral-like fashion, with the center portion and the legs being co-planar in the undeflected state. During use, the clip is rotated, drawing tissue into the center portion. Systems incorporating the clip are also provided.

22 Claims, 12 Drawing Sheets

(56) References Cited

U.S. PATENT DOCUMENTS

| | | | |
|---|---|---|---|
| 5,203,787 A * | 4/1993 | Noblitt et al. | 606/232 |
| 5,242,457 A * | 9/1993 | Akopov et al. | 606/144 |
| 5,454,834 A * | 10/1995 | Boebel et al. | 606/228 |
| 5,478,354 A * | 12/1995 | Tovey et al. | 606/219 |
| 5,810,882 A * | 9/1998 | Bolduc et al. | 606/213 |
| 6,080,182 A * | 6/2000 | Shaw et al. | 606/213 |
| 6,171,320 B1 * | 1/2001 | Monassevitch | 606/151 |
| 6,391,038 B2 | 5/2002 | Vargas et al. | |
| 6,491,707 B2 | 12/2002 | Makower et al. | |
| 6,551,319 B2 * | 4/2003 | Lieberman | 623/17.11 |
| 6,776,784 B2 * | 8/2004 | Ginn | 606/151 |
| 7,112,207 B2 | 9/2006 | Allen et al. | |
| 7,220,268 B2 | 5/2007 | Blatter | |
| 2002/0183786 A1 * | 12/2002 | Girton | 606/213 |
| 2004/0153101 A1 * | 8/2004 | Bolduc et al. | 606/143 |
| 2004/0220596 A1 * | 11/2004 | Frazier et al. | 606/153 |
| 2004/0225300 A1 | 11/2004 | Goldfarb et al. | |
| 2006/0064116 A1 | 3/2006 | Allen et al. | |
| 2006/0276871 A1 * | 12/2006 | Lamson et al. | 623/1.11 |
| 2007/0073337 A1 | 3/2007 | Abbott et al. | |
| 2007/0270905 A1 * | 11/2007 | Osborne | 606/213 |
| 2008/0004640 A1 * | 1/2008 | Ellingwood | 606/151 |

\* cited by examiner

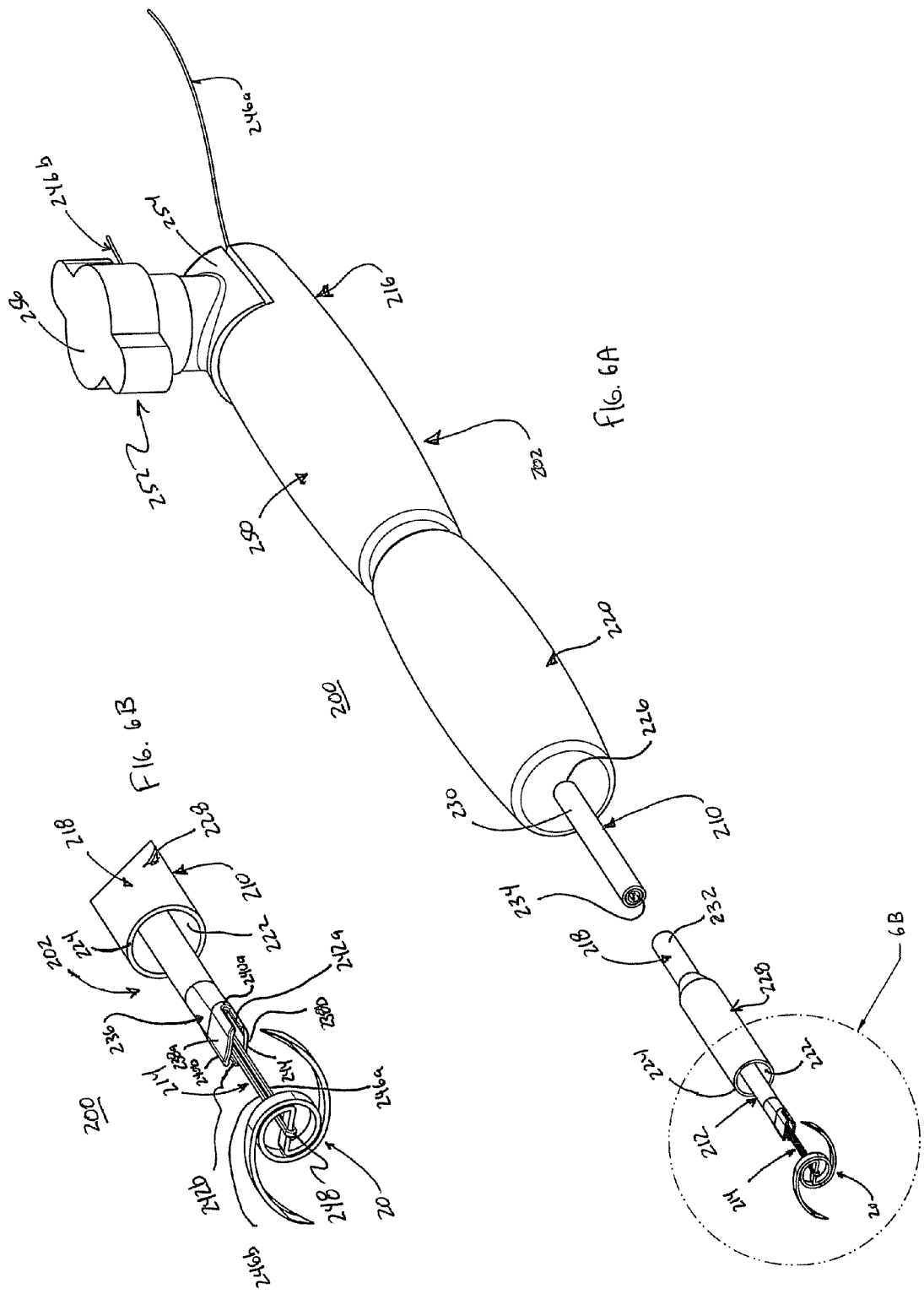

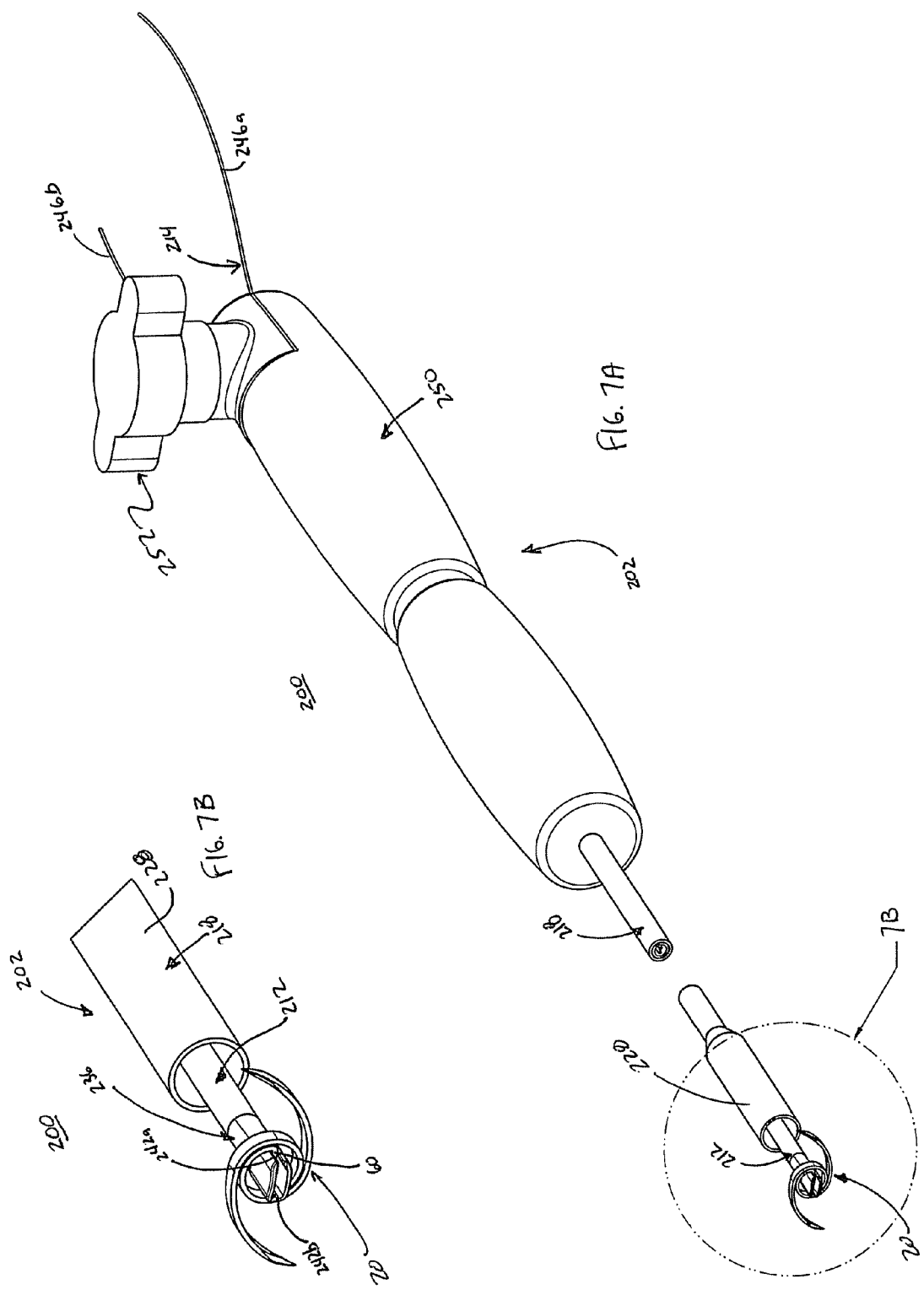

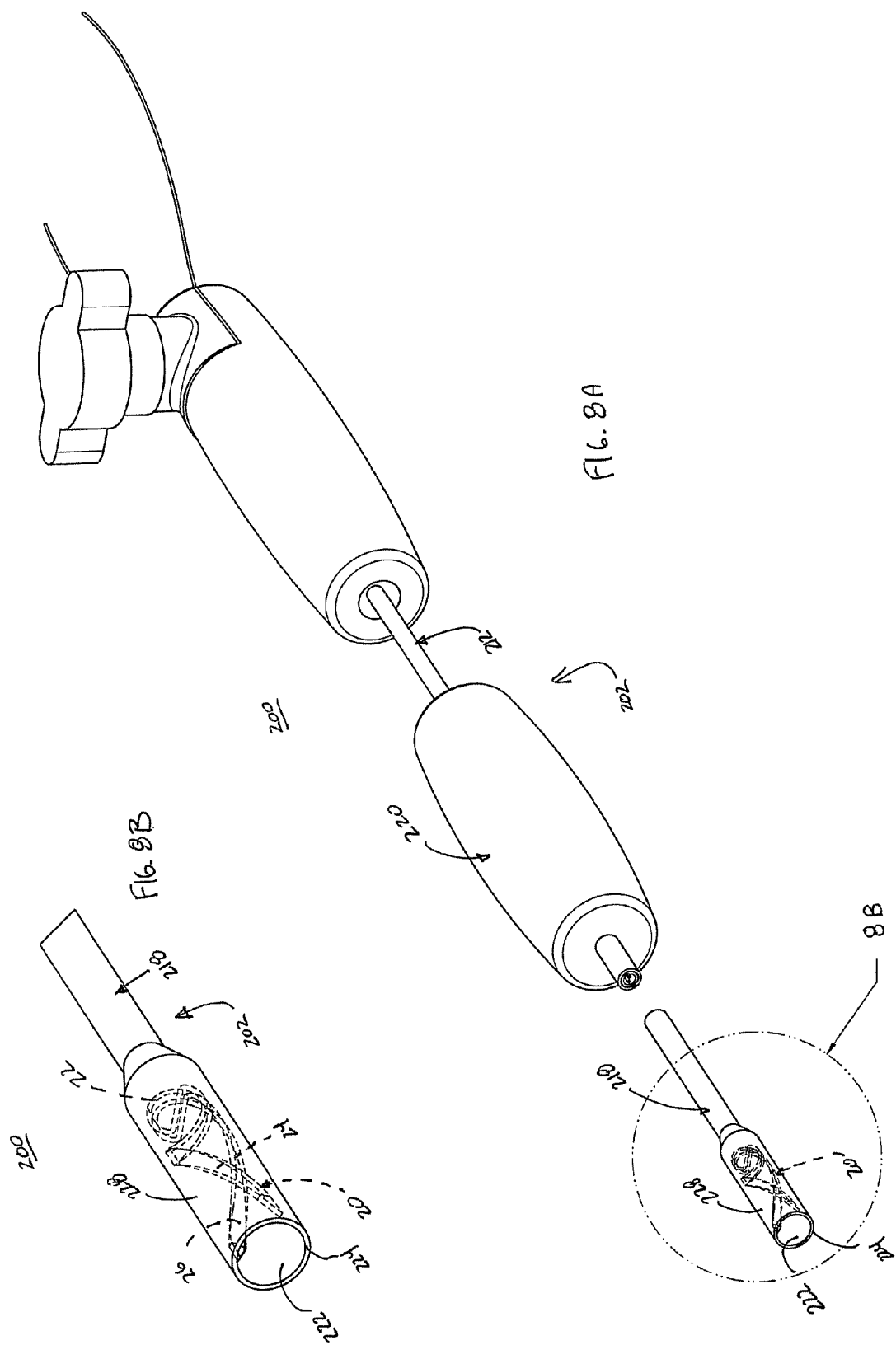

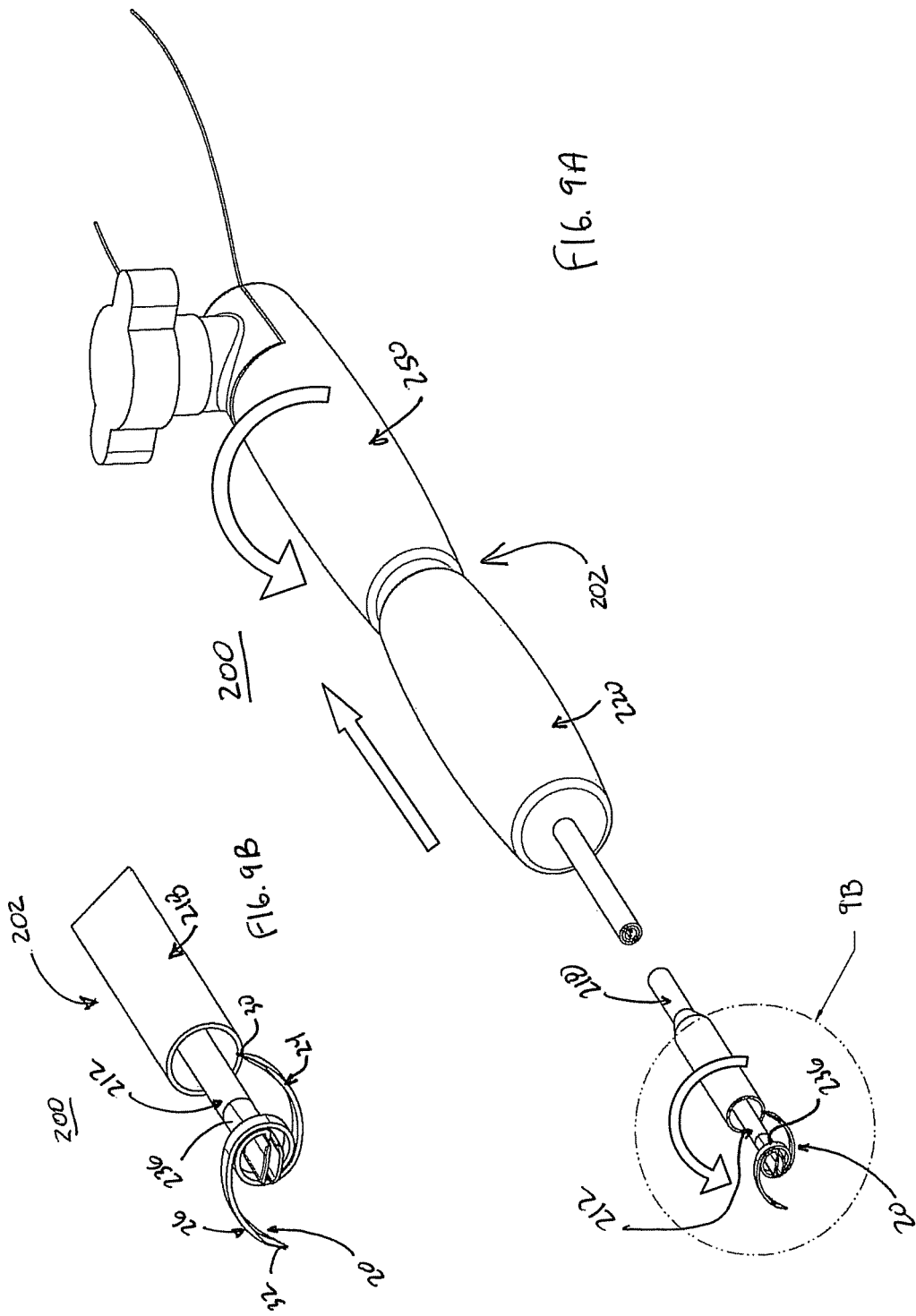

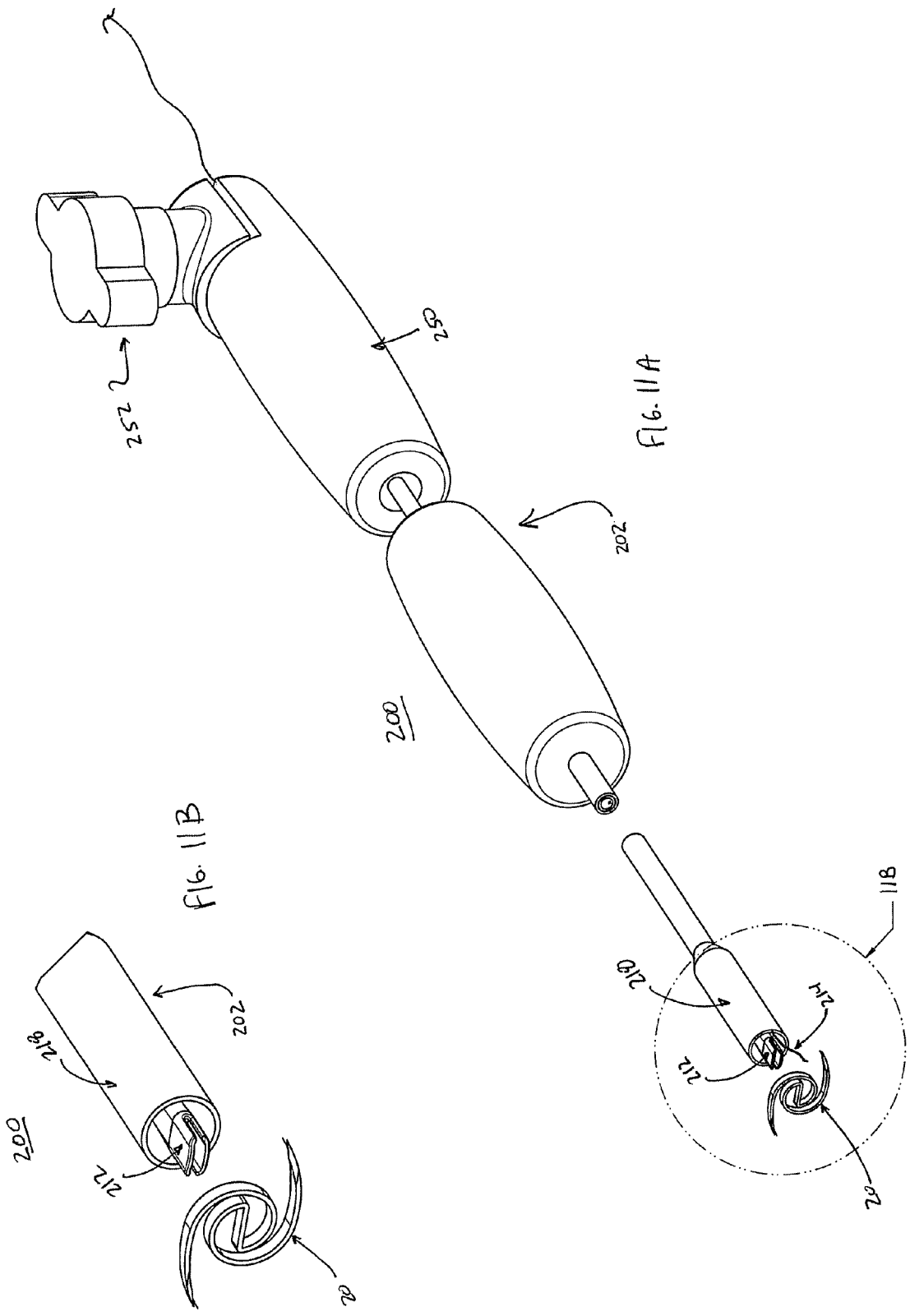

SURGICAL FASTENING CLIPS, SYSTEMS AND METHODS FOR PROXIMATING TISSUE

BACKGROUND

The present disclosure relates generally to apparatus and methods for surgically proximating tissue, such as in closing a patent foramen ovale or other tissue defect.

The need to surgically proximate and attach segments of tissue arises under a plethora of different circumstances. Tissue defects, such as wounds, are one such example. Treatment of a skin surface wound typically entails suturing edges of the wound together. In many instances, however, the tissue defect to be treated is internally located, and thus not readily accessible by a surgeon otherwise attempting to utilize a conventional suture thread to effectuate repair of the defect. Access to internal tissue defects of these types through invasive surgery introduces a high level of risk that can result in serious complications for the patient, especially where the tissue defect is located at or near a vital organ. One example of an internal tissue defect of this type is a patent foramen ovale ("PFO") that can occur between the left and right atria of the heart.

By way of reference, during development of a fetus in utero, most of the fetus' circulation is shunted away from the lungs through vessels or foramens that are open during fetal life. Normally, these specialized vessels and foramens will close shortly after birth. One such opening is known as the foramen ovale that allows blood to pass directly from the right atrium to the left atrium, thus bypassing the lungs. Following birth, and with establishment of pulmonary circulation, the increased left atrial blood flow and pressure results in the functional closure of the foramen ovale, followed by formation of an anatomical seal with continued development of the heart.

In some instances, the foramen ovale fails to entirely close. This condition, known as PFO, may allow blood to continue to shunt between the left and right atria, posing potentially serious health risks. Other septal tissue defects can also occur and require treatment.

Invasive surgical procedures can be performed to address the septal tissue defects described above, as well as multiple other internal tissue defects. Alternatively, less invasive procedures, such as catheter-based procedures, have been suggested. In the context of PFO treatment, for example, expandable umbrella- or disk-like devices are delivered, via catheter, into the heart. Generally, the device is inserted through the natural opening of the defect, and the expandable structures are deployed to secure or bring together tissue segments surrounding the defect.

Alternatively, other internal tissue defect repair and/or tissue proximation techniques have been suggested in which a clip formed from a super elastic material is provided. The clip is self-transitionable from a deflected state in which the clip (or segments thereof) is at least somewhat linear, to an undeflected state in which the clip has a coiled curvature, thereby drawing opposing ends of the clip more closely to one another. During use, the clip is deployed, in the deflected state, to the defect site via a catheter or other minimally invasive apparatus. Upon deployment from the delivery tool, the clip reverts to the undeflected state or shape, with opposing ends or tips of the clip piercing through the tissue segments, pulling or proximating the segments into contact with one another. For example U.S. Pat. No. 6,776,784 describes that, in repairing a PFO, the clip ends are pierced through septum wall segments. The clip is then allowed to self-transition toward its natural or undeflected state (W-shape). This action, in turn, draws the tissue segments toward one another, serving to at least partially close the PFO. While viable, suggested clip configurations, and related applications, may not provide consistent, long-term closure of the defect. Similar concerns may also arise in the context of other tissue proximation or plication procedures, such as anastomosis, etc.

In light of the above, a need exists for improved devices, systems, and methods for surgically proximating tissue, for example closing tissue defects such as a PFO or other internal tissue defect.

SUMMARY

Some aspects in accordance with principles of the present disclosure relate to a surgical fastener clip for surgically proximating tissue, such as in repairing a tissue defect. The surgical clip provides an undeflected state in which the clip comprises a center portion, a first leg, and a second leg. The center portion has a perimeter defining a circle-like shape. The first leg projects outwardly relative to this perimeter from a point of departure to a tip. This projection establishes a spacing between the first leg and the perimeter. The second leg similarly projects outwardly relative to the perimeter from a point of departure to a tip, with a spacing being established between the second leg and the perimeter. With this in mind, extension of each of the legs relative to the perimeter defines a wind direction that is either clockwise or counterclockwise, with the legs having identical wind directions. For example, the wind direction of both of the legs is clockwise or is counterclockwise. In some configurations, the clip further comprises a linear cross-member extending across the perimeter. In other embodiments, the center portion and the legs combine to form the surgical clip as having a hurricane-like shape. In yet other configurations, the surgical clip is formed by a wire that is partially wound onto itself in a spiral-like fashion, with the center portion and the legs being co-planar in the undeflected state. Regardless, the surgical clip facilitates surgical proximation of tissue (e.g., repair of a tissue defect) by rotating the surgical clip in a direction causing engaged tissue to gather between each of the legs and a corresponding region of the perimeter, as well as within the center portion.

Yet other aspects in accordance with principles of the present disclosure relate to a system for surgically proximating tissue. The system includes a surgical fastener clip and a clip delivery device. The surgical clip provides an undeflected state in which the clip includes a center portion, a first leg, and a second leg. The center portion has a perimeter defining a circle-like shape, with the first and second legs projecting outwardly relative to this perimeter in establishing a spacing between each of the legs and the perimeter. In this regard, extension of each of the legs relative to the perimeter defines a clockwise or counterclockwise wind direction, with the wind directions of the legs being identical. The clip delivery device includes a sheath assembly and a retainer. The sheath assembly includes a sheath sized to slidably receive the surgical clip, and the retainer is slidably disposed within the sheath. A distal region of the retainer is configured to selectively engage the clip. With this in mind, the system is configured to provide a pre-deployment state in which the clip is releasably assembled to the distal region of the retainer, and the distal region and the clip are disposed within the sheath. In the pre-deployment state, the clip is collapsed from the undeflected state to a collapsed state. During use, upon deployment of the clip from the sheath, the clip naturally transitions from the collapsed state toward the undeflected state. In some embodiments, the sheath is akin to a catheter such that the surgical clip can be deployed in a minimally invasive manner. In other embodiments, the delivery device further includes a tether, such as a suture, selectively retaining the clip relative to the distal region of the retainer.

Yet other aspects in accordance with principles of the present disclosure relate to a method for surgically proximating tissue. The method includes providing a surgical fastener clip having an undeflected state in which the clip includes a center portion having a perimeter defining a circle-like shape, along with first and second legs projecting outwardly relative to the perimeter. The legs extend in identical wind directions relative to the perimeter. The surgical clip is assembled to a delivery device otherwise including a retainer and a sheath. In this regard, the clip is selectively engaged by a distal region of the retainer, and is disposed within the sheath. With this assembly, the sheath maintains the clip in a collapsed state. The clip is advanced, in the collapsed state, to a location adjacent the tissue to be proximated. The clip is transitioned from the collapsed state toward the undeflected state, for example by releasing the clip from the sheath. The clip is rotated via the retainer such that the tips pierce through the tissue to be proximated. The clip is further rotated via the retainer, such that the tissue is gathered between each of the legs and a corresponding region of the center portion to at least partially proximate the tissue. The clip is released from the delivery device. In some embodiments, the method is performed in closing a PFO, with the clip being advanced through the patient's vasculature.

BRIEF DESCRIPTION OF THE DRAWINGS

FIG. 6A is a perspective view of a tissue proximating system in accordance with principles of the present disclosure, including the clip of FIG. 1A and a clip delivery device;

FIG. 6B is an enlarged, perspective view of a distal portion of the system of FIG. 6A;

FIGS. 7A-8B illustrate assembly of the system of FIG. 6A to a pre-deployment state;

FIG. 9A is a perspective view of the system of FIG. 6A, illustrating deployment of the clip from the delivery device;

FIG. 9B is an enlarged, perspective view of a distal portion of the system of FIG. 9A;

FIG. 11A is a perspective view of the system of FIG. 6A, illustrating release of the clip from the delivery device;

FIG. 11B is an enlarged, perspective view of a portion of the system of FIG. 11A.

DETAILED DESCRIPTION

Figure 1A:
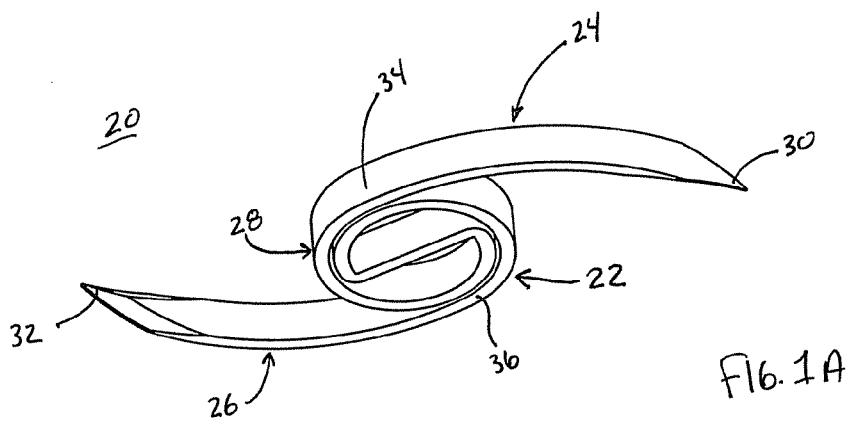
FIG. 1A is a perspective view of a surgical fastener clip in accordance with principles of the present disclosure in an undeflected state.
Figure 1B:
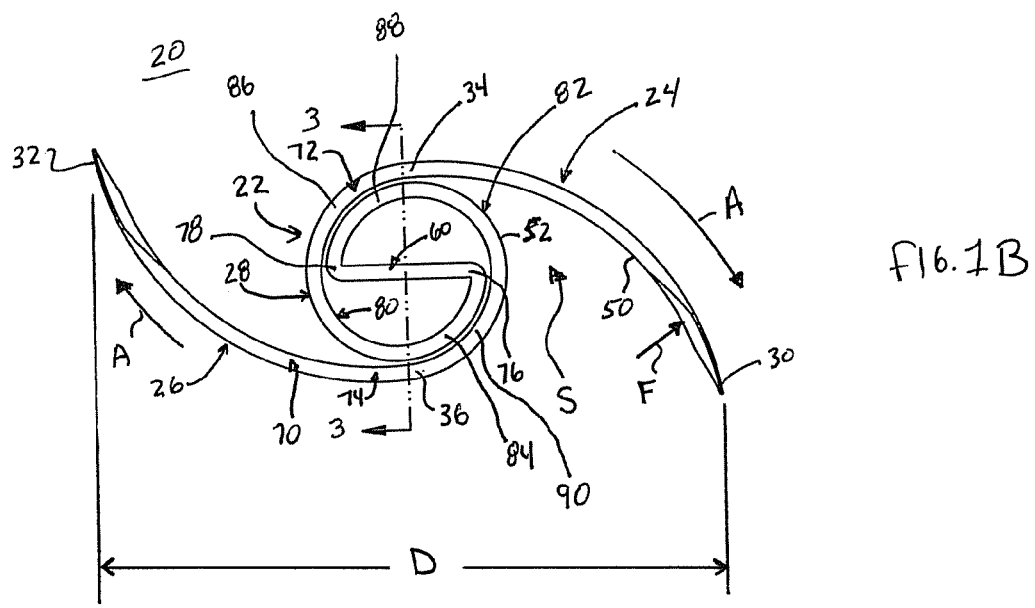
FIG. 1B is a top plan view of the clip of FIG. 1A.

FIGS. 1A and 1B illustrates one configuration of a surgical fastener clip 20 in accordance with principles of the present disclosure for use in surgically proximating tissue, for example closing an internal tissue defect. As a point of reference, the clip 20 is shown in a relaxed or undeflected state in FIGS. 1A and 1B. During use, and as described below, the surgical clip 20 is deflectable or collapsible from the undeflected state of FIGS. 1A and 1B to a collapsed state, and will self-revert from the collapsed state to or toward the undeflected state. With this in mind, in at least the undeflected state, the clip 20 includes or defines a center portion 22, a first leg or prong 24, and a second leg or prong 26. Details on the components are provided below. In general terms, however, the center portion 22 has a perimeter 28 defining a circular or circle-like shape. The legs 24, 26 project outwardly relative to the perimeter 28, with the first leg 24 terminating at a tip 30, and the second leg 26 terminating at a tip 32. In this regard, the legs 24, 26 extend in or with an identical wind direction, such that the clip 20 has, in some embodiments, a hurricane-like shape (as best reflected by the top plan view of FIG. 1B).

The wind direction associated with each of the legs 24, 26 is either clockwise or counterclockwise relative to the circle-like shape of the perimeter 28. The perimeter 28 may or may not be continuous, and may or may not reflect a true circle; relative to a two-dimensional top (or bottom) plan view, however, the perimeter 28 of the center portion 22 establishes a basis from which clock-type directional attributes (e.g., wind direction) can be identified. For example, the first leg 24 extends from the perimeter 28 at a point of departure 34, terminating at the tip 30. The point of departure 34 can be defined as a point along the leg 24 at which a lateral spacing between the leg 24 and the perimeter 28 begins to increase. By way of clarification, the point of departure 34 is at approximately a 12 o'clock position of the perimeter 28 relative to the orientation of FIG. 1B. With these conventions in mind, FIG. 1B depicts the first leg 24 as establishing a wind direction (represented by the arrow "A") that is clockwise. Extension of the second leg 26 relative to the perimeter 28 from a point of departure 36 similarly defines the same clockwise wind direction A. Alternatively, the wind direction established by both of the legs 24, 26 can be counterclockwise.

In some embodiments, the legs 24, 26 can have an identical construction/dimensions. Thus, the legs 24, 26 can define an identical curvature in extension from the perimeter 28. Alternatively, the legs 24, 26 can have differing dimensions and/or curvatures. Similarly, one or both of the legs 24, 26 can have a linear segment or be entirely linear (i.e., extend tangentially from the perimeter 28). Regardless, the wind direction A of the legs 24, 26 are identical.

As best shown in FIG. 1B, the legs 24, 26 are in some embodiments, positioned opposite one another relative to the perimeter 28. Thus, the point of departure 34 of the first leg 24 is opposite the point of departure 36 of the second leg 26. Stated otherwise, relative to an imaginary line intersecting the perimeter 24 and a center point of the center portion 22, the clip 22 is symmetrical. In other embodiments, however, the legs 24, 26 can be non-uniformly spaced about the perimeter 28 (e.g., relative to the conventions of FIG. 1B, the point of departure 36 of the second leg 26 can be located at a point other than the 6 o'clock position shown). In yet other embodiments, three or more of the legs 24, 26 can be provided that may or may not be equidistantly spaced about the perimeter 28.

The center portion 22 and the legs 24, 26 are, in some embodiments, co-planar in the undeflected state. That is to say, and with additional reference to FIG. 1C, the legs 24, 26 extend in a plane defined by a face 40 of the center portion 22, such that the clip 20 does not exhibit a three-dimensional spiral or corkscrew attribute. Alternatively, however, the legs 24, 26 can be constructed to project out of a plane of the center portion 22 in the undeflected state.

The clip 20 is constructed such that the legs 24, 26 elastically resist movement away from the perimeter 28, both axially and radially relative to the perimeter 28. For example, a radial or lateral spacing S is defined between an inner surface 50 of the first leg 24 and a region 52 of the perimeter 28 closest to the inner surface 50. As a point of reference, relative to any one point along the inner surface 50, a minimum lateral spacing S is established relative to the closest, adjacent point along the perimeter 28, with this minimum lateral spacing S increasing from the point of departure 34 to the tip 30. With this in mind, the affinity of the first leg 24 to resist laterally outward movement relative to the perimeter 28 is characterized by the leg resisting a force tending to increase the lateral spacing S. In other words, a force (generically represented by an arrow "F" in FIG. 1B) exerted or experienced along the inner surface 50 tends to cause the first leg 24 to move in a direction opposite the wind direction A. Construction of the clip 20 causes the first leg 24 to resist this unwinding-type force. Instead, the first leg 24 (as well as the second leg 26) slightly deflects in response to the force F, causing material (such as tissue) within the lateral spacing S to gather or pinch between the inner surface 50 and the region 52 of the perimeter 28 as described below.

Figure 2B:
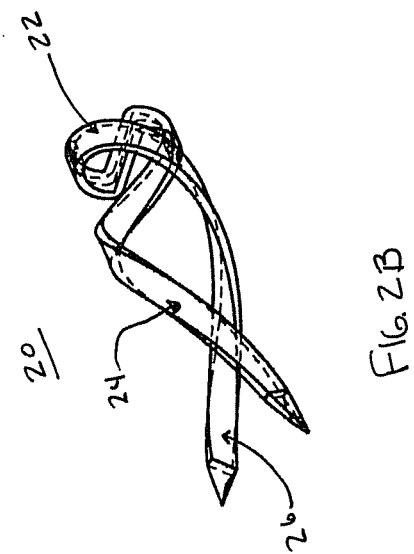
FIG. 2B is a perspective view of another collapsed state of the clip of FIG. 1A.
Figure 2A:
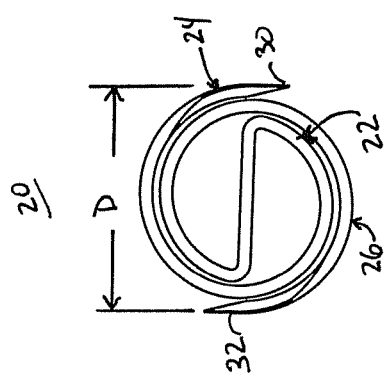
FIG. 2A is a top plan view of the surgical clip of FIG. 1A in a collapsed state.

In the undeflected state of FIG. 1B, a maximum outer dimension D of the clip 20 is defined as a linear distance between the first and second tips 30, 32. The outer dimension D can vary, and is selected in accordance with the particular procedure(s) for which the clip 20 will be used. For example, for PFO closure applications, the tip-to-tip distance D can be on the order of 1 cm, thereby ensure sufficient tissue interface within a PFO tunnel, otherwise having a typical diameter of 1-19 mm. Alternatively, other maximum outer dimensions D are also acceptable. Regardless, the clip 20 is collapsible from the undeflected state to a collapsed state in which the maximum dimension D is greatly reduced. For example, FIG. 2A illustrates one collapsed state of the clip 20 in which the legs 24, 26 have been forced to wrap onto the center portion 22. Alternatively, FIG. 2B illustrates a differing collapsed state of the clip 20 in which the legs 24, 26 are forced longitudinally away from the center portion 22, as well as circumferentially collapsed toward one another. Other collapsed states can also be provided. In any of the collapsed states, the maximum dimension D (referenced in FIG. 2A, for example) of the clip 20 is reduced as compared to the maximum dimension D in the undeflected state, such that the collapsed clip 20 is more readily delivered to a confined surgical site, such as via a catheter or similar body as described below. Further, upon removal of the force(s) otherwise causing the clip 20 to the collapsed state, the clip 20 self-reverts back to the undeflected state of FIG. 1A.

An ability of the clip 20 to self-revert from a collapsed state to the undeflected state is provided, in some embodiments, by forming the clip 20 from an elastic material, such as stainless steel, and in other embodiments, a super elastic material such as a shape memory alloy, for example Nitinol. Alternatively, other biocompatible elastic or super elastic materials can also be employed. Along these lines, in some embodiments, the clip 20 is formed of a bioresorbable material that, following closure of the tissue defect or other tissue proximation, will slowly dissolve over time. Alternatively or in addition, the clip 20 can include a biocompatible coating that promotes tissue healing and/or can contain a drug or therapeutic agent that releases over time.

Returning to FIGS. 1A and 1B, in some embodiments, the clip 20 further includes or forms a linear cross-member 60 extending within the circular-like perimeter 28. The cross-member 60 can assume a variety of forms, and in some embodiments is configured for interface with a delivery device (described below) to facilitate transfer of a torque or rotational force applied to the cross-member 60 to the center portion 22 and the legs 24, 26. With the one example configuration of FIGS. 1A and 1B, the cross-member 60 is centrally positioned within the circle-shape perimeter 28, and bisects an imaginary line connecting the points of departure 34, 36. With this but one acceptable configuration, a torque or rotational moment force applied to the cross-member 60 is relatively uniformly distributed onto the center portion 22 and thus onto each of the arms 24, 26. Alternatively, the cross-member 60 can be asymmetrically positioned relative to the arms 24, 26 and/or can assume a variety of other configurations. In other embodiments, the clip 20 (along with a corresponding delivery device) are configured to effectuate assembly and force transmission in a manner not otherwise requiring a cross-member such that the cross-member 60 can be eliminated.

In some embodiments, the clip 20 is formed by a single wire 70 the ends or tips 30, 32 of which are sharpened for piercing tissue. The wire 70 is partially wound onto itself during manufacture to define a cross-member segment (i.e., the cross-member 60), a first section 72, and a second section 74. The cross-member 60 has or is defined by opposing, first and second ends 76, 78. The first section 72 extends from the first end 76 and is wound (in a single wind direction, for example clockwise relative to FIG. 1B) to define a first segment 80 and the first leg 24. More particularly, the first segment 80 extends from the first end 76 of the cross-member 60 and forms a portion of the perimeter 28. The first leg 24 extends from the first segment 80. With this in mind, the first segment 80 has, in some embodiments, a relatively uniform radius of curvature (slightly increasing from the first end 76), with this radius of curvature being less than a radius of curvature defined by the first leg 24. As a point of reference, while the point of departure 34 has been designated relative to the perimeter 28, the wound form of the first section 72 also identifies the point of departure 34 as being a location along a length of the wire 70 at which the wound radius of curvature significantly increases (e.g., greater than 25 percent). The second section 74 extends from the second end 78 in a similar manner (and identical wind direction), defining a second segment 82 and the second leg 26. In some embodiments, the first and second sections 72, 74 are identical. Thus, a radius of curvature of the second segment 82 is less than a radius of curvature of the second leg 26, with the point of departure 36 being defined as a location along a length of the wire 70 where the radius of curvature significantly increases.

Winding of the first and second segments 80, 82 is such that the segments 80, 82 partially circumferentially overlap one another in a spiral-like manner. For example, the first segment 80 can be defined as having a leading region 84 and a trailing region 86. Similarly, the second segment 82 can be defined as having a leading region 88 and a trailing region 90. As shown, in the undeflected state, a portion of the trailing region 86 of the first segment 80 circumferentially overlaps (i.e., is radially outside of) a portion of the leading region 88 of the second segment 72. Similarly, a portion of the trailing region 90 of the second segment 82 circumferentially overlaps a portion of the leading region 84 of the first segment 80. With this construction, as the first leg 24 is forced away from the perimeter 28 (i.e., unwound), a slight circumferential gap will be formed (or an existing gap will be enlarged) between the trailing region 86 of the first segment 80 and the leading region 88 of the second segment 82. Similarly, a circumferential gap is created and/or expanded between the trailing region 90 of the second segment 82 and the leading region 84 of the first segment 80 with forced movement of the second leg 26 away from the perimeter 28. As described below, these gaps effectively serve as pathways for forced gathering of tissue within the center portion 22 in connection with a tissue proximation procedure.

Figure 3:
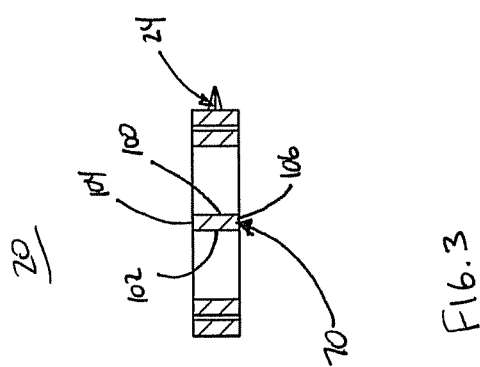
FIG. 3 is a cross-sectional view of the clip of FIG. 1B along the lines 3-3.

The wire 70 useful for forming the clip 20 as described above can assume a variety of forms. In some embodiments, the wire 70 is flattened. For example, as shown in FIG. 3, the continuous wire 70 defines opposing major faces 100, 102, and opposing sides 104, 106. The opposing major faces 100, 102 each define a width that is greater than a width (i.e., thickness) defined by the sides 104, 106. It has surprisingly been found that a flat wire (e.g., dimensions on the order of 0.010 inch×0.030 inch) greatly reduces undesired deviation of the legs 24, 26 from a perpendicular orientation. In other embodiments, however, a round wire (i.e., circular in cross-section) can be employed. Similarly, two or more separately formed wires can be assembled to one another in forming the clip 20. Even further, the clip 20 can be formed by component(s) other than a wire.

Figure 1C:
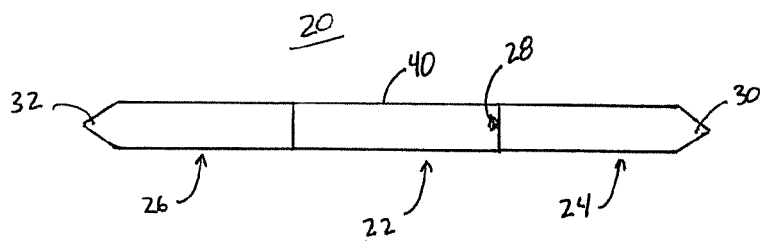
FIG. 1C is a side view of the clip of FIG. 1A.
Figure 4:
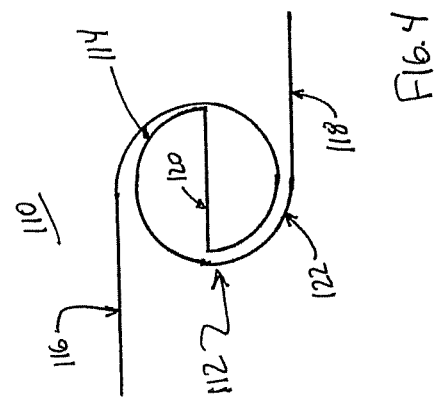
FIG. 4 is a simplified top plan view of an alternative surgical fastener clip in accordance with principles of the present disclosure.

In addition to the component(s) employed in forming the clip 20, the shape of the clip 20 can vary from that described and shown in FIGS. 1A-1C. For example, an alternative surgical fastener clip 110 in accordance with principles of the present disclosure is shown in FIG. 4. The clip 110 is akin to the clip 20 (FIG. 1A) previously described, and in the undeflected state of FIG. 4 includes a center portion 112 having or defining an approximately circular-shaped perimeter 114 from which first and second legs 116, 118 project. As compared to the clip 20, the legs 116, 118 extend in a substantially tangential fashion relative to a circumference of the circle-like perimeter 114, and are relatively linear (relative to the top plan view of FIG. 4). However, extension of the legs 116, 118 relative to the perimeter 114 defines a wind direction, with the wind direction for both of the legs 116, 118 being identical (i.e., counterclockwise relative to the orientation of FIG. 4). Further, the clip 110 includes an optional cross-member 120. As with previous embodiments, the clip 110 can be formed from a single, continuous wire 122 that is wound in a manner defining the center portion 112, the legs 116, 118, and the cross-member 120.

Figure 5A:
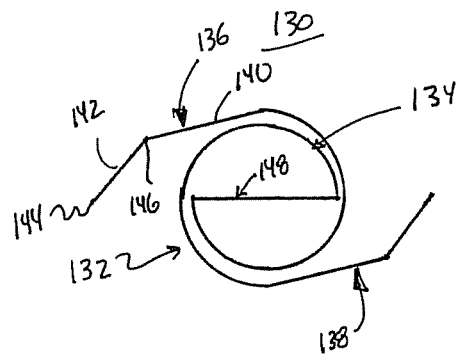
FIG. 5A is a simplified top plan view of another surgical fastener clip in accordance with principles of the present disclosure.
Figure 5B:
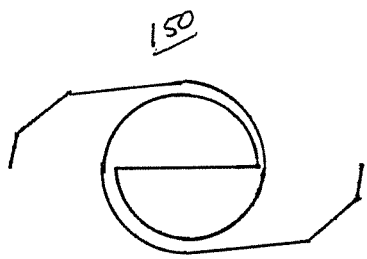
FIG. 5B is a simplified top plan view of another surgical fastener clip in accordance with principles of present disclosure.

Yet another configuration of a surgical fastener clip 130 in accordance with principles of the present disclosure is provided in FIG. 5A. As with previous embodiments, the clip 130 includes a center portion 132 defining a substantially circle-like perimeter 134 from which first and second legs 136, 138 extend. Extension of each of the legs 136, 138 establishes a wind direction relative to the circular perimeter 134, with the wind directions of the legs 136, 138 being identical (e.g., counterclockwise relative to the orientation of FIG. 5A). In this regard, each of the legs 136, 138 includes a trailing region 140 and a leading region 142. The trailing region 140 extends in a substantially linear, tangential fashion relative to a circumference of the perimeter 134. The leading region 142 extends from the trailing region 140, and terminates at a tip 144, with a bend 146 being formed at a transition from the trailing region 140 to the leading region 142. The bend 146 (and difference of curvature, if any, between the regions 140, 142) promote a more gradual introduction of tissue into the center portion 132 as described below. Finally, in some constructions, the clip 130 includes an optional cross-member 148 extending within the circular perimeter 134. While the legs 136, 138 are shown as each forming the single bend 146, in other embodiments, a plurality of bends can be imparted, for example as shown with the alternative surgical fastener clip 150 of FIG. 5B.

Figure 5C:
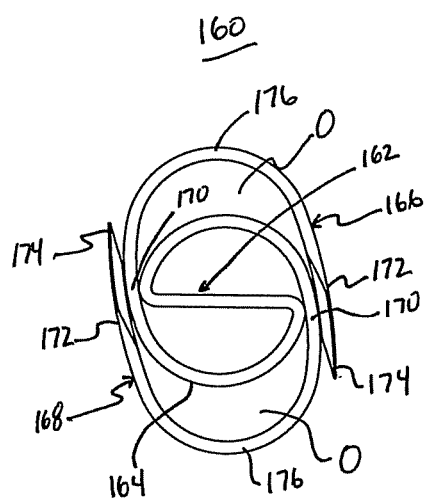
FIG. 5C is a top plan view of another surgical fastener clip in accordance with principles of the present disclosure.

Yet another configuration of a surgical fastener clip 160 in accordance with principles of the present disclosure is shown in FIG. 5C. As with previous embodiments, the clip 160 includes a center portion 162 defining a substantially circle-like perimeter 164 from which first and second legs 166, 168 extend. Extension of the legs 166, 168 establishes a wind direction relative to the circular perimeter 164, with the wind directions of the legs 166, 168 being identical (e.g., clockwise relative to the orientation of FIG. 5C). In this regard, each of the legs 166, 168 includes a trailing region 170 and a leading region 172 terminating at a tip 174. In the relaxed state or undeflected state of FIG. 5C, the leading region 172 rests against the center portion 162 and/or the trialing region 170 of the opposite leg 166, 168 (e.g., in FIG. 5C, the leading region 172 of the first leg 166 rests against the trailing region 170 of the second leg 168 and the center portion 162), generating an opening O between an intermediate region 176 of each leg 166, 168 and the perimeter 164. During use, a delivery device (not shown) acts to force (e.g., mechanically push) the leading regions 172 away from the center portion 162 to create gaps within which tissue to be proximated is gathered.

Regardless of an exact construction of the surgical fastener clip, other aspects of the present disclosure relate to a delivery device for delivering the clip to, and manipulating the clip at, an internal region of a patient. With this in mind, one example of a system 200 including a delivery device 202 in accordance with the principles of the present disclosure is shown in FIG. 6A. As a point of reference, FIG. 6A illustrates the delivery device 202 along with the surgical clip 20 in a partially-assembled state, with the delivery device 202 and the clip 20 combining to define the system 200 for proximating tissue (e.g., closing an internal tissue defect). In general terms, the delivery device 202 is akin to a catheter-type device, and is configured to selectively maintain the clip 20 in a collapsed state (it being understood that the clip 20 is shown in the undeflected state in FIG. 6A), as well as placement and manipulation of the clip 20 during use.

In some embodiments, the delivery device 202 includes a sheath assembly 210, a retainer 212, an optional tether 214, and a handle assembly 216. Details on the components 210-216 are provided below. In general terms, the sheath assembly 210 includes a sheath 218 sized to slidably receive the clip 20. The retainer 212 is slidably disposed within the sheath 218 and is configured to selectively retain the clip 20, for example in conjunction with the tether 214. The handle assembly 216 maintains the retainer 212 and the tether 214 relative to the sheath assembly 210, and facilitates transmission of a user-applied force onto the retainer 212, and thus onto the clip 20 when the clip 20 is otherwise engaged with the retainer 212. With this configuration, the retainer 212 and the tether 214 retain the clip 20 both within and distal the sheath 218. Further, the handle assembly 216 allows a user to manipulate the clip 20 in a desired fashion (e.g., rotate) as described below.

The sheath assembly 210 includes the sheath 218 and a hub 220. The hub 220 is mounted to the sheath 218 and provides a user with a convenient surface for manipulating the sheath 218 in a desired fashion.

The sheath 218 can be akin to a catheter, sized for insertion into a blood vessel or other bodily lumen. Alternatively, the sheath 218 can have larger dimensions (e.g., akin to a cannula for laparoscopic or other minimally invasive applications). The sheath 218 is thus a tubular body defining a lumen 222 extending from a distal end 224 to a proximal end 226 (referenced generally in FIG. 6A). The lumen 222 is open at the distal end 224 and is optionally open at the proximal end 226 for receiving the retainer 212. Alternatively, a radial port can be formed for accessing the lumen 222. In some configurations, a distal section 228 of the sheath 218 has a slightly enlarged diameter as compared to a proximal section 230 (and in some embodiments as compared to an intermediate section 232). Regardless, a diameter of the lumen 222 at the distal section 228 is sized to force and maintain the clip 20 at a desired outer dimension (i.e., collapsed state) appropriate for advancement through the patient's vasculature (or other pathway) as described below. Thus, at least the distal section 228 of the sheath 218 exhibits sufficient circumferential structural strength or integrity to maintain the clip 20 in the desired collapsed state without failure.

The sheath 218 can be formed from a variety of biocompatible materials exhibiting sufficient flexibility for traversing a patient's vasculature in a substantially atraumatic manner for septal defect applications. In some embodiments, the distal section 228 can be formed of a more rigid material as compared to a remainder of the sheath 218 to better force and maintain the clip 20 in the collapsed state. For example, the distal section 228 can be formed of stainless steel or other metal, whereas a remainder of the sheath 218 is formed of a more flexible material, such as a polymeric braided tube. Alternatively, the sheath 218 can be a homogenous body.

The hub 220 is mounted to the proximal end 226 of the sheath 218, and can assume a variety of forms and sizes. In general terms, the hub 220 serves as a handle or grip for a user to easily grasp, facilitating user manipulation of the sheath 218 (e.g., to effectuate distal or proximal sliding movement of the sheath 218 relative to the retainer 212). Thus, the hub 220 can form a longitudinal bore (not shown) through which the retainer 212 is slidably received.

The retainer 212 is an elongated body, at least a portion of which is sized to be slidably received within the lumen 222 of the sheath 218. In some configurations, the retainer 212 is tubular, forming a central passage 234 through which the tether 214 is received. With specific reference to FIG. 6B, a distal region 236 of the retainer 212 is configured to selectively engage the clip 20. For example, in some embodiments, the distal region 236 is partially flattened (relative to an initially round, circular shape in transverse cross-section) to define opposing side walls 238a, 238b, and opposing end walls 240a, 240b. Slots 242a, 242b (the slot 242b being partially visible in FIG. 6B) are formed in the opposing end walls 240a, 240b, respectively. The slots 242a, 242b are axially open at a distal end 244 of the distal region 236, and extend through a thickness of the corresponding end wall 240a or 240b. Thus, where the retainer 212 is formed as a tubular body, the slots 242a, 242b are open to the passageway 234. With this construction, the slots 242a, 242b are sized to receive a corresponding portion of the clip 20 as described below. The slots 242a, 242b are but one acceptable configuration for providing desired selective connection of the retainer 212 with the clip 20. A wide variety of other constructions are also acceptable, so long as a sufficient connection with the clip 20 is achieved for transmitting a torque from the retainer 212 onto the clip 20.

The distal region 238 can be separately formed and subsequently assembled to a remainder of the retainer 212. For example, the distal region 238 can be formed of a more rigid material amenable to formation of the slots 242a, 242b during manufacture (e.g., stainless steel, Nitinol, etc.), whereas a remainder of the retainer 212 is formed of a more flexible material, such as a braid-reinforced polymer tube. With this but one acceptable construction, the retainer 212 is sufficiently compliant for traversing a tortuous pathway (e.g., a patient's vasculature), yet exhibits sufficient structural strength for transmitting an applied torque onto the clip 20. Alternatively, the retainer 212 can be formed as an integral, homogenous body so long as a torqueable attribute is provided (e.g., a rotational force applied at a proximal end of the retainer 212 is transmitted to the distal end 244).

The optional tether 214 is, in some embodiments, a continuous suture or other thread extending through the passageway 234 of the retainer 212 (and thus through the sheath 218). As described below, the tether 214 selectively engages the clip 20, for example by wrapping about a corresponding segment of the clip 20. Thus, in the partially assembled state of the system 200 in FIGS. 6A and 6B, the tether 214 is arranged to effectively define first and second sections 246a, 246b that extend through the retainer 212 and the handle assembly 216, interconnected by a wrapped portion 248 (FIG. 6B) that is threaded about a component of the clip 20. As a point of reference, FIGS. 6A and 6B illustrate the tether sections 246a, 246b as being linear or rigid distal the retainer 212 for ease of illustration; when the tether 214 is a suture, the segments 246a, 246b, and in fact the tether 214 as a whole, are entirely flexible. Alternatively, other constructions of the tether 214 can be employed; in yet other configurations of the delivery device 202, the tether 214 can be eliminated.

The handle assembly 216 includes a handle 250 and a locking device 252. The handle 250 is mounted to a proximal end (not shown) of the retainer 212, and provides a grip surface for a user to apply a torque to the retainer 212. With this configuration, then, the retainer 212 extends through the hub 220 that is otherwise mounted to the sheath 218. The locking device 252 is optionally provided, and is movably associated with the handle 250. In particular, the locking device 252 is configured to selectively capture or lock the tether 214 and includes, in some embodiments, a locking plate 254 and an actuator 256. More particularly, the locking device 252 is constructed and assembled to the handle 250 such that the locking plate 254 is moved relative to the handle 250 via operation (e.g., rotation) of the actuator 256, facilitating a tight engagement of the tether 214 between the locking plate 254 and the handle 250. Operation of the actuator 256 in an opposite direction releases the locking plate 254 relative to the handle 250, and thus allows the tether 214 to be freely manipulated relative to other components of the delivery device 202. Alternatively, the locking device 252 can assume a wide variety of other forms appropriate for locking and releasing the tether 214. Further, with embodiments in which the tether 214 is eliminated, the locking device 252 can also be eliminated.

Upon final assembly of the delivery device 202, the retainer 212 is slidably disposed within the sheath 218. Further, the retainer 212 extends through the hub 220, such that the hub 220, as well as the sheath 218, is longitudinally slidable over the retainer 212 (and thus the retainer 212 is axially slidable within the sheath 218 and the hub 220). Prior to assembly of the clip 20 to the delivery device 202, the tether 214 is not fully disposed within the retainer 212 in the manner reflected in FIGS. 6A and 6B. For example, while the first section 246a may be loaded or threaded through the retainer 212 and the handle 250, an entirety of the second section 246b extends distal the distal end 244 of the retainer 212 for subsequent assembly about the clip 20 as described below.

The above-described system 200 can be assembled in various manner. In some embodiments, assembly of the clip 20 to the delivery device 202 initially entails axially manipulating the retainer 212 and the sheath 218 relative to one another such that the distal region 236 of the retainer 212 extends distal the distal end 224 of the sheath 218. For example, the hub 220 is maneuvered proximally toward the handle 250 (or vice-versa) to the position of FIG. 6A. The clip 20 is positioned distal the distal region 236, and the tether 214 mounted to the clip 20. More particularly, the second section 246b is wrapped about the cross-member 60 to form the wrapped portion 248, and then fed proximally through the passageway 234 of the retainer 212 such that both segments 246a, 246b are proximal the handle 250 as shown, with the locking device 252 in a released state.

The clip 20 is then maneuvered such that the cross-member 60 is aligned with and then received or nested within the slots 242a, 242b. The tether 214 is tensioned (e.g., the sections 246a, 246b are pulled proximally) so as to more firmly retain the clip 20 within the distal region 236, as shown in FIGS. 7A and 7B. The tether 214 is then locked to the handle 250 via operation of the locking device 252 as described above. Once locked, the tether 214 applies a constant, proximal tension or force onto the clip 20, thereby capturing the clip 20 relative to the retainer 212.

With the clip 20 loaded to the retainer 212, the delivery device 202 is then manipulated to position the clip 20 within the distal section 228 of the sheath 218. For example, and with reference to FIGS. 8A and 8B, the hub 220 is distally moved along the retainer 212 (or vice-versa), directing the distal end 224 of the sheath 218 to contact and then pass over the clip 20. As the clip 20 is forced into the lumen 222 with further distal movement of the sheath 218 relative to the retainer 212, the distal section 228 directs or forces the clip 20 to transition from the undeflected state (FIG. 7B) to a collapsed state (FIG. 8B). In the collapsed state, an effective maximum outer dimension of the clip 20 is reduced to a distance or dimension defined by the diameter of the lumen 222 at the distal section 228. To assist in loading the clip 20 within the sheath 218, the retainer 212, and thus the clip 20 attached thereto, can be rotated. Further, while the collapsed state of the clip 20 in FIG. 8B reflects an axial deflection of the legs 24, 26 relative to the center portion 22 (e.g., the legs 24, 26 extend distal the center portion 22), in other embodiments, loading of the clip 20 can entail tightly wrapping the legs 24, 26 against the center portion 22 (e.g., the collapsed state of FIG. 2A). As a point of reference, the delivery device 202 can be alternatively constructed to effectuate loading of the clip 20 within the sheath 218 in a variety of other manners, for example, via proximal movement of the retainer 212 relative to the sheath 218. Regardless, in the pre-deployment state of the system 200 in FIGS. 8A and 8B, the clip 20 is collapsed to a size appropriate for internal bodily deployment, for example for passage through a patient's vasculature. The system 200 can then be operated by a surgeon in performing a tissue proximation procedure.

Several non-limiting examples of tissue proximation procedures using the system 200 are described below. In general terms, however, upon placement of the distal end 224 of the sheath 218 at a desired location, the delivery device 202 is operated to position the clip 20, and thus the distal region 236 (FIG. 7B) of the retainer 212, distal the distal end 224 of the sheath 218. For example, and as shown in FIGS. 9A and 9B, the hub 220 is moved proximally toward the handle 250, such that the clip 20 is distally beyond or outside of the sheath 218. To assist in deploying the clip 20 from the sheath 218, the retainer 212, and thus the clip 20, can be rotated (e.g., approximately 180°). Regardless, once free of the confines of the sheath 218, the clip 20 will self-revert to the undeflected state. If it is determined that the clip 20 is not positioned at a desired location relative to the tissue to be proximated, the clip 20 can be collapsed back into the sheath 218, and the sheath 218 then re-located as desired.

Figure 10B:
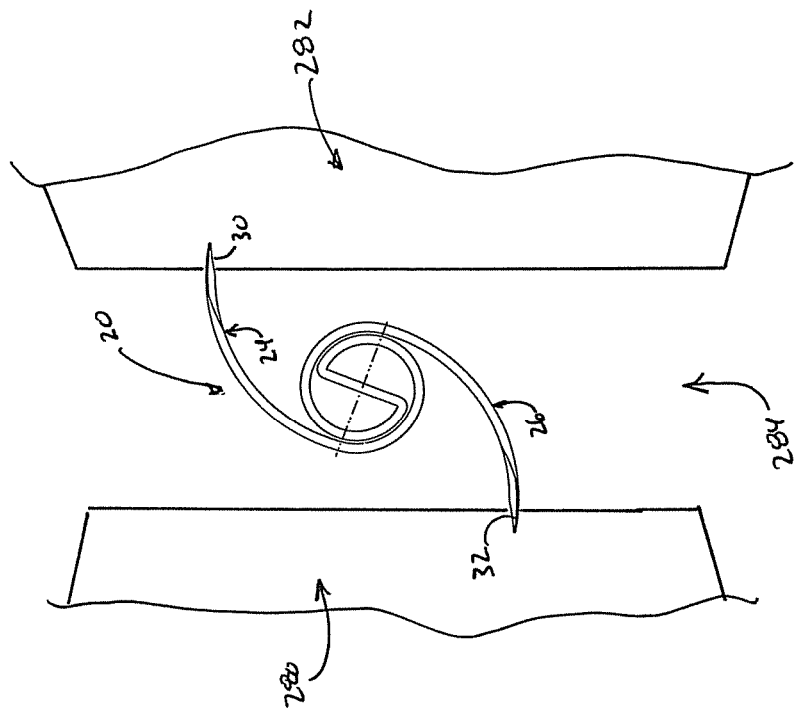
FIGS. 10A-10D illustrate, in simplified schematic form, use of the clip of FIG. 1A to proximate tissue in accordance with principles of the present disclosure.
Figure 10A:
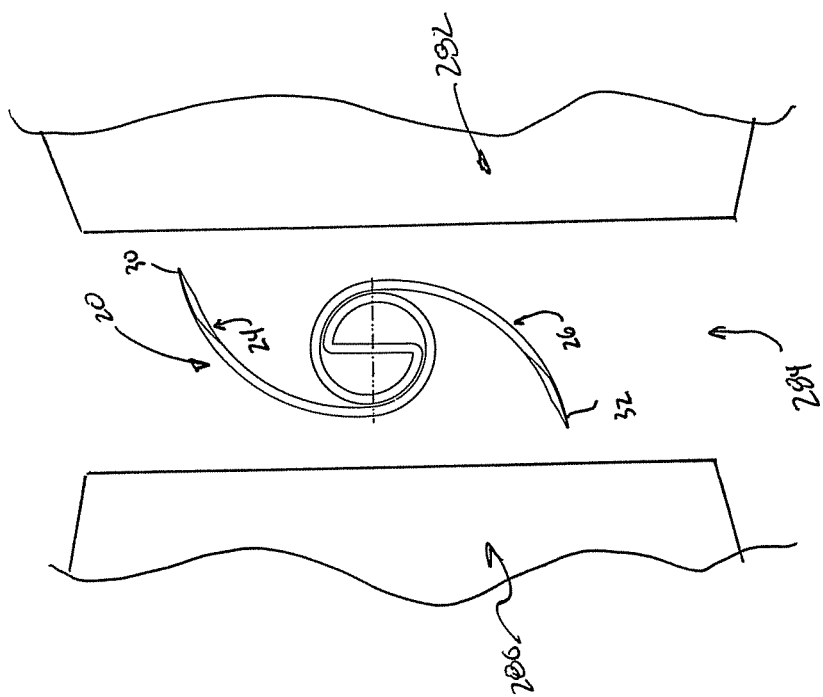
Figure 10D:
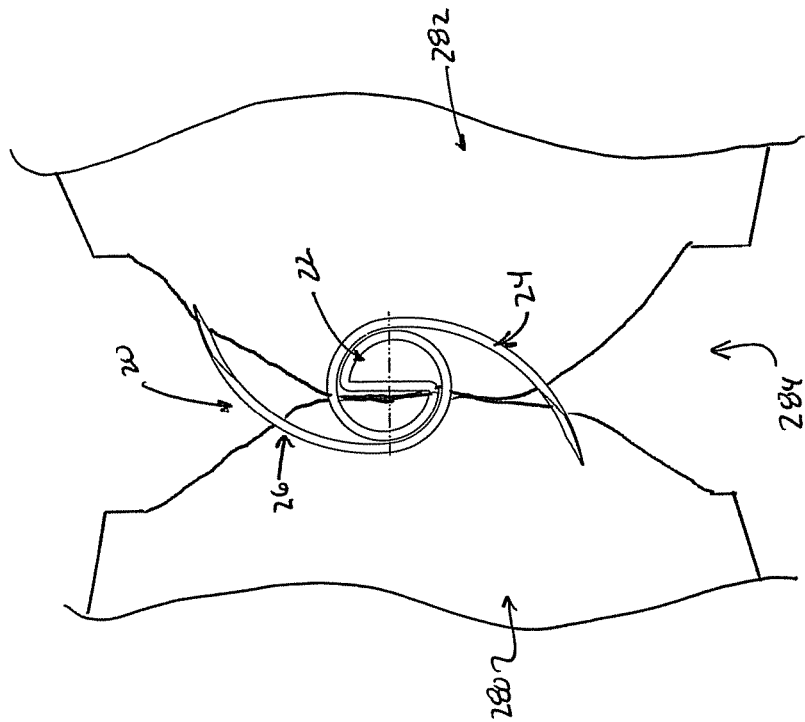
Figure 10C:
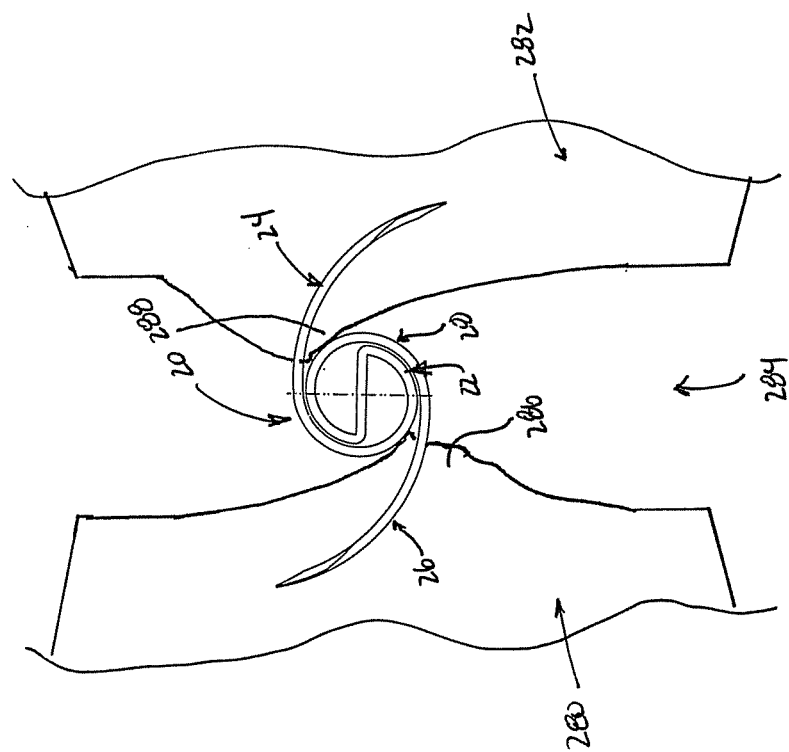

Once deployed from the sheath 218, the clip 20 is rotated via rotation of the handle 250 and thus the retainer 212 to engage desired tissue segment(s). In particular, a user-applied torque at the handle 250 is transmitted to the clip 20 due to continued engagement with the distal region 236. Rotation of the clip 20 in the wind direction of the legs 24, 26 causes the tips 30, 32 to engage or pierce into tissue otherwise in contact with the tips 30, 32. For example, FIG. 10A schematically illustrates opposing tissue segments 280, 282 separated by a spacing 284 within which the clip 20 is initially deployed. With initial rotation of the clip 20 (in the wind direction of the legs 24, 26, for example clockwise relative to the orientation of FIG. 10A), the tips 30, 32 pierce into respective ones of the tissue segments 280, 282 as shown in FIG. 10B. With further rotation of the clip 20, the legs 24, 26 continually pass through an increasing volume of the tissue segments 280, 282, gathering or pinching portions 286, 288 of the tissue segments 280, 282, respectively, between the legs 24, 26 and the center portion 22, including the perimeter 28, as shown in FIG. 10C. Gaps between the legs 24, 26 and the perimeter 28 effectively serve as pathways, guiding or drawing tissue toward the center portion 22. With even further rotation of the clip 20, additional amounts of the tissue segments 280, 282 are forced between the legs 24, 26 such that the tissue segments 280, 282 become gathered within the center portion 22 as shown in FIG. 10D. Thus, following rotation of the clip 20 to a desired extent, the tissue segments 280, 282 are drawn together or proximated to close, and in some embodiments seal, the spacing 284.

Once desired rotation of the clip 20 is complete, the clip 20 is released from the delivery device 202. For example, and as shown in FIGS. 11A and 11B, the locking device 252 is operated to release the tether 214. The tether 214 is then removed from engagement (e.g., un-wrapped) with the clip 20, for example by pulling one of the tether sections 246a or 246b (FIG. 6A) proximally from the handle 250. Once the tether 214 is released from the clip 20, the delivery device 202 can then be retracted away from the clip 20. If necessary, the sheath 218 can be distally advanced to push against the clip 20 to assist in removal of the retainer 212 from the clip 20.

Figure 12A:
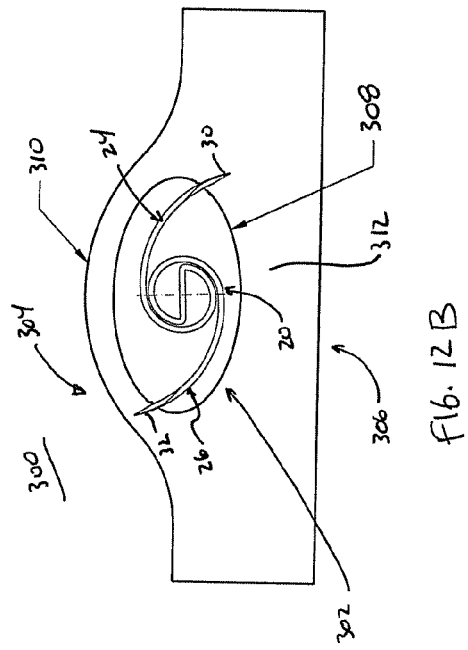
FIGS. 12A-12C illustrate, in simplified form, repair of a PFO in accordance with principles of the present disclosure.

As indicated above, the surgical fastener clip and related delivery devices and systems can be used for performing a plethora of different tissue proximation procedures. In some aspects of the present disclosure, the surgical clips and related systems are highly useful for repairing internal tissue defects or tissue openings in or about various bodily organs, including vascular applications. In one non-limiting example, the present disclosure is useful in repairing a PFO. In this regard, FIG. 12A provides a simplistic, cross-sectional representation of an anatomical structure of a human heart 300 having a PFO 302. The PFO 302 is a region defined between a left atrium 304 and a right atrium 306 of the heart 300. In this regard, the PFO 302 is generally referred to as a tunnel 308 formed between or by a septum primum 310 of the left atrium 304 and a septum secundum 312 of the right atrium 306. The septum primum 310 is a flap-like structure, with the tunnel 308 allowing blood to shunt between the right atrium 306 and the left atrium 304.

Figure 12B:
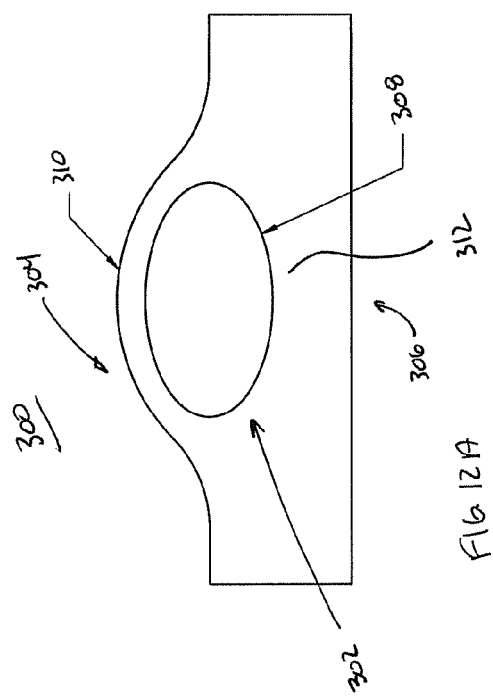
Figure 12C:
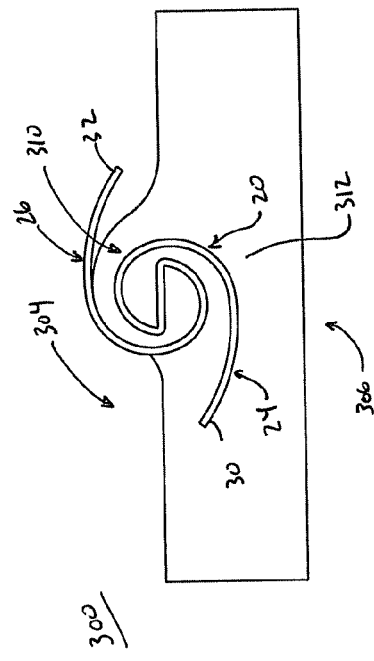

Repair of the PFO 302 in accordance with aspects of the present disclosure includes deploying the loaded system 200 (FIG. 8A) as previously described and then delivering and deploying the clip 20 within the tunnel 308 as shown in FIG. 12B. Desired positioning of the clip 20 within the tunnel 308 can be confirmed, where desired, by various techniques such as fluoroscopy. Upon deployment, the clip 20 is rotated in the wind direction of the legs 24, 26 (e.g., clockwise relative to the orientation of FIG. 12B) such that the clip tips 30, 32 pierce through tissue of the septum primum 310 and septum secundum 312. With further rotation of the clip 20, the engaged tissue is gathered or drawn within the clip 20, resulting in closure of the tunnel 308 as generally shown in FIG. 12C. More particular, the septal tissue 310, 312 is gathered and tightly held within the clip 20, thereby sealing the tunnel 308. Over time, the gathered tissue will heal or otherwise experience inter-growth, resulting in a more complete seal.

The PFO repair methodology described above is but one useful application of the present disclosure. In other embodiments, the clips, systems, and methods of the present disclosure can be employed in performing other tissue defect repair procedures. Even further, other surgical applications such as tubal ligation, vasectomy, varicocele repair, GERD surgeries, etc., can also benefit from the present disclosure. Essentially, any surgical procedure entailing proximating or plicating an area of loose tissue and creating a seal can be accomplished with the present disclosure. Even further, a tubular device (e.g., catheter or stent) can be carried by the delivered surgical fastener clip of the present disclosure, and effectively implanted or held in place upon engagement of the clip with surrounding tissue. The tissue is sealed against the tubular device via the clip, thereby facilitating various procedures such as, for example, bladder repair, feeding tube placement, sphincter repair, bile duct drainage, etc. Further, the clips, systems, and methods can be employed in performing a valve leaflet apposition procedure in which the surgical fastener clip of the present disclosure is deployed to pull and hold two heart valve leaflets together, effectively emulating an Alfieri stitch used for addressing valve (e.g., mitral valve) regurgitation. For example, it has been found that surgical fastener clips of the present disclosure can be deployed to penetrate tissue of adjacent leaflets via the opposing tip ends, respectively, and/or by deploying the surgical fastener clip of the present disclosure so as to surround the chordae from each leaflet and pull them together.

Although the present disclosure has been described with reference to preferred embodiments, workers skilled in the art will recognize that changes can be made in form and detail without departing from the spirit and scope of the present disclosure.

What is claimed is:

1. A system for surgically proximating tissue, the system comprising:
    a surgical fastener clip providing an undeflected state in which a single wire of the clip defines:
    a center portion having a perimeter defining a circle-like shape,
    a first leg projecting relative to the perimeter from a point of departure to a tip to establish a spacing between the first leg and the perimeter,
    a second leg projecting relative to the perimeter from a point of departure to a tip to establish a spacing between the second leg and the perimeter,
    wherein extension of each of the legs relative to the perimeter defines a wind direction that is one of clockwise and counterclockwise, the wind directions being identical; and
    a clip delivery device including:
    a sheath assembly including a sheath sized to slidably receive the clip,
    a retainer slidably disposed within the sheath and including a distal region configured to selectively engage the clip, wherein the retainer is an elongated tube,
    a tether disposed within the retainer;
    wherein in a pre-deployment state of the system, the tether is releasably mounted to the clip, the clip is releasably assembled to the distal region of the retainer, and the distal region and the clip are disposed within the sheath, the clip being collapsed from the undeflected state to a collapsed state.

2. The system of claim 1, wherein the tether is a suture.

3. The system of claim 2, wherein the clip delivery device further includes a locking device configured to selectively retain the suture.

4. The system of claim 1, wherein the clip further includes a linear cross-member extending within the perimeter, and further wherein the distal region of the retainer forms at least one slot sized to slidably receive the linear cross-member.

5. The system of claim 1, wherein the delivery device further includes a handle assembly maintaining the sheath and the retainer such that the sheath is axially slidable relative to the retainer and the retainer is rotatable relative to the sheath.

6. The system of claim 5, wherein the system is configured to provide a deployment state in which the clip is positioned distal the sheath and the retainer is rotatable relative to the sheath via the handle assembly to apply a rotational torque onto the clip.

7. The system of claim 1, wherein at least a distal section of the sheath is formed of metal.

8. The system of claim 7, wherein the distal section of the sheath defines an inner diameter that is less than a lateral spacing between the tips of the clip in the undeflected state such that upon insertion of the clip into the distal section of the sheath, the sheath forces the clip to the collapsed state.

9. The system of claim 8, wherein in the undeflected state, the legs are co-planar with the central portion, and in the collapsed state, the legs and the central portion are not co-planar.

10. The system of claim 9, wherein the clip is configured to self-revert from the collapsed state to the undeflected state.

11. The system of claim 1, wherein the system is configured for closing a septal defect.

12. A method for surgically proximating tissue, the method comprising:
    providing a surgical fastener clip having an undeflected state in which a single wire of the clip defines:
    a center portion having a perimeter defining a circle-like shape,
    a first leg projecting relative to the perimeter from a point of departure to a tip to establish a spacing between the first leg and the perimeter,
    a second leg projecting relative to the perimeter from a point of departure to a tip to establish a spacing between the second leg and the perimeter,
    wherein extensions of each of the legs relative to the perimeter defines a wind direction that is one of clockwise and counterclockwise, the wind directions being identical;
    assembling the clip to a delivery device including a retainer, a tether and a sheath, wherein the retainer is slidably disposed within the sheath, wherein the retainer is an elongated tube, wherein the tether is disposed within the retainer, wherein the clip is selectively engaged by a distal region of the retainer and the clip is disposed within the sheath, the sheath maintaining the clip in a collapsed state, wherein the tether is releasably mounted to the clip;

advancing the clip, in the collapsed state, to a location adjacent tissue to be proximated;

releasing the clip from the sheath to allow the clip to transition from the collapsed state toward the undeflected state;

rotating the clip via the retainer such that the tips pierce through tissue to be proximated;

further rotating the clip via the retainer such that tissue to be proximated is gathered between each of the legs and a corresponding region of the center portion to at least partially proximate the tissue; and releasing the clip from the delivery device.

13. The method of claim 12, wherein assembling the clip to the delivery device includes:

providing the clip in the undeflected state;

positioning the clip distal the sheath; and moving one of the sheath and the clip relative to an other of the sheath and the clip such that the clip is disposed within the sheath;

wherein the sheath forces the clip to transition from the undeflected state to the collapsed state with the movement.

14. The method of claim 12, wherein the distal region of the retainer forms a slot, the slot being open at a distal end, and further wherein assembling the clip to the delivery device includes sliding a portion of the clip within the slot.

15. The method of claim 12, wherein the sheath is axially slidable relative to the retainer, and further wherein transitioning the clip from the collapsed state includes axially sliding one of the sheath and the retainer relative to an other of the sheath and the retainer.

16. The method of claim 12, wherein rotating the clip includes applying a torque to the retainer.

17. The method of claim 12, wherein the sheath is a catheter.

18. The method of claim 12, wherein rotating the clip includes continuously rotating the clip in one of a clockwise and a counterclockwise direction to effectuate an increasing amount of tissue being gathered within the clip.

19. The method of claim 12, wherein rotating the clip includes rotating the clip in the wind direction of the legs.

20. The method of claim 12, wherein rotating the clip includes forcing tissue into the center portion of the clip.

21. The method of claim 12, wherein the method relates to closing of a PFO, and further wherein advancing the clip includes positioning the clip in a tunnel formed between a septum secundum of a right atrium and a septum primium of a left atrium.

22. The method of claim 12, wherein the method relates to valve leaflet apposition, and further wherein rotating the clip includes one of:

piercing tissue of the valve leaflets with the tips, and surrounding chordae of the valve leaflets and drawing the valve leaflets together.

\* \* \* \* \*